(12) United States Patent
Goehring et al.

(10) Patent No.: US 7,288,658 B2
(45) Date of Patent: Oct. 30, 2007

(54) PROCESS FOR PREPARATION OF PYRIDINE DERIVATIVES

(75) Inventors: Wolfgang Goehring, Steinen (DE); Peter John Harrington, Louisville, CO (US); Lewis M Hodges, Longmont, CO (US); David A Johnston, Louisville, CO (US); Goesta Rimmler, Bad Krozingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 537 days.

(21) Appl. No.: 10/888,912

(22) Filed: Jul. 9, 2004

(65) Prior Publication Data

US 2005/0014792 A1   Jan. 20, 2005

(30) Foreign Application Priority Data

Jul. 15, 2003 (EP) ................................ 0301559

(51) Int. Cl.
*C07D 401/02* (2006.01)
*C07D 213/02* (2006.01)

(52) U.S. Cl. ................ 546/317; 544/60; 544/124; 544/360

(58) Field of Classification Search ................ 546/317; 544/60, 124, 360
See application file for complete search history.

(56) References Cited

U.S. PATENT DOCUMENTS

| | | | |
|---|---|---|---|
| 4,745,123 A | 5/1988 | Butler et al. | |
| 4,764,361 A | 8/1988 | Bilski et al. | |
| 5,387,595 A | 2/1995 | Mills et al. | |
| 5,554,633 A | 9/1996 | Teall | |
| 5,612,337 A | 3/1997 | Baker et al. | |
| 5,719,147 A | 2/1998 | Dorn et al. | |
| 5,972,938 A | 10/1999 | Rupniak | |
| 6,294,537 B1 | 9/2001 | Bichon et al. | |
| 6,297,375 B1 | 10/2001 | Bös et al. | |
| 6,479,483 B2 | 11/2002 | Bös et al. | |

FOREIGN PATENT DOCUMENTS

| | | |
|---|---|---|
| EP | 089 765 | 9/1983 |
| EP | 0 235 663 | 9/1987 |
| EP | 244 080 | 11/1987 |
| EP | 244 937 | 11/1987 |
| EP | 359 547 | 3/1990 |
| EP | 385 350 | 9/1990 |
| EP | 405 931 | 1/1991 |
| EP | 427 526 | 5/1991 |
| EP | 524 781 | 1/1993 |
| EP | 638 557 | 2/1995 |
| EP | 0 733 632 | 9/1996 |
| EP | 1 035 115 | 9/2000 |
| EP | 1 103 545 | 5/2001 |
| EP | 1 103 546 | 5/2001 |
| ES | 2 029 801 | 10/1992 |
| GB | 1 557 420 | 12/1979 |
| KR | 8101320 | 10/1981 |
| KR | 8101697 | 10/1981 |
| WO | WO92/06080 | 4/1992 |
| WO | WO93/11110 | 6/1993 |
| WO | WO94/21611 | 9/1994 |
| WO | WO94/27604 | 12/1994 |
| WO | WO95/16679 | 6/1995 |
| WO | WO95/18124 | 7/1995 |
| WO | WO95/23798 | 9/1995 |
| WO | WO96/00213 | 1/1996 |
| WO | WO95/33744 | 12/1996 |
| WO | WO97/19926 | 6/1997 |
| WO | WO97/36871 | 10/1997 |
| WO | WO98/21185 | 5/1998 |
| WO | WO 00/50398 | 8/2000 |
| WO | WO 02/08232 A1 | 1/2002 |

OTHER PUBLICATIONS

Barker, Reviews in the Neurosciences, vol. 7, No. 3, pp. 187-214 (1996).
Longmore et al., Can. J. Physiol. Pharmacol., vol. 75, pp. 612-621 (1977).
Kramer et al., Science, vol. 281, pp. 1640-1645 (1998).
Maggi et al., J. Auton Pharmacol., vol. 13, pp. 23-93 (1993).
Navari et al., New England Journal of Medicine, vol. 340(3), pp. 190-195 (1999).
Abstract corresponding to WO 96/00213.
Abstract corresponding to WO 94/27604.
Ikeura et al., Chem. Phar. Bull., vol. 45(10), pp. 1642-1652 (1997).
Natsurgari et al., J. Med. Chem., vol. 38(16), pp. 3106-3120 (1995).
Abstract corresponding to WO 98/21185.
Katritzky, A. R. et al., J. C. S. Perkin I, 1981 pp. 1180-1185.
Hosoki R. et al., European Journal of Pharmacology vol. 341, pp. 235-241 (1998).

*Primary Examiner*—Zinna N. Davis
(74) *Attorney, Agent, or Firm*—George W. Johnston; Patricia S. Rocha-Tramaloni; Kimberly J. Prior

(57) ABSTRACT

The present invention relates to a process for the manufacture of compounds of formula

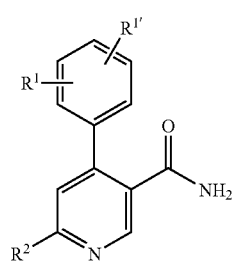

I wherein the substituents are as described herein which comprises the steps of
a) reacting a compound of formula

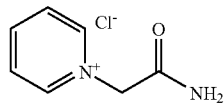

X with a compound of formula

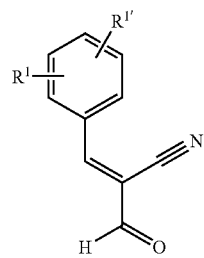

XIII to form a compound of formula

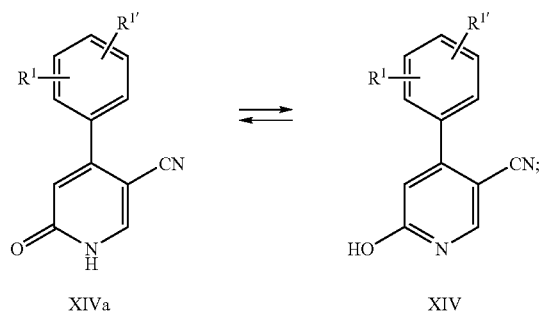

b) converting the OH/=O function of compounds of formula XIV/XIVa into a leaving group P with a reagent containing a leaving group, selected from $POCl_3$, $PBr_3$, MeI and $(F_3CSO_2)_2O$ to form a compound of formula

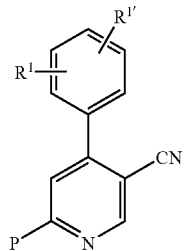

XV wherein P is halogen or trifluoromethanesulfonate;
c) substituting $R^2$ for the leaving group P by reacting compound XV with $HR^2$ to form a compound of formula

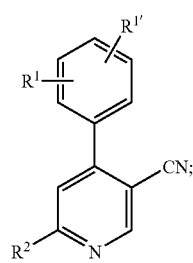

XVI and
d) hydrolyzing the nitrile function in an acidic medium selected from $H_2SO_4$, HCl and acetic acid, to form a compound of formula I

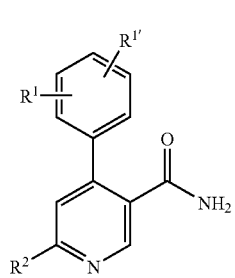

I

The compounds of formula I are valuable intermediates for the manufacture of therapeutically active compounds which have NK-1 antagonist activity.

25 Claims, No Drawings

PROCESS FOR PREPARATION OF PYRIDINE DERIVATIVES

FIELD OF THE INVENTION

The present invention relates to processes for the preparation of pyridine derivatives.

BACKGROUND OF THE INVENTION

Compounds of formula II are therapeutically active compounds

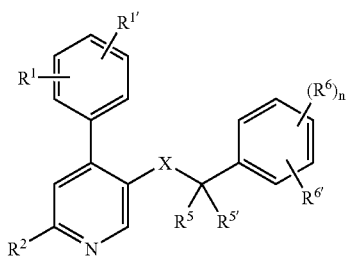

wherein
$R^1$ and $R^{1'}$ are each independently hydrogen, lower alkyl, alkoxy, halogen, cyano or alkylamino;
$R^2$ is —$N(R^3)_2$, —$N(R^3)(CH_2)_nOH$, —$N(R^3)S(O)_2$-lower alkyl, —$N(R^3)S(O)_2$-phenyl, —$N=CH-N(R^3)_2$, —$N(R^3)C(O)R^3$ or a cyclic tertiary amine of the formula

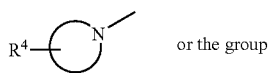 or the group

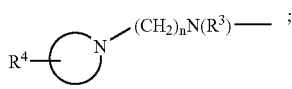 ;

each $R^3$ is independently hydrogen, $C_{3-6}$-cycloalkyl, benzyl or lower alkyl;
$R^4$ is hydrogen, hydroxy, lower alkyl, —$(CH_2)_n$COO-lower alkyl, —$N(R^3)$CO-lower alkyl, hydroxy-lower alkyl, cyano, —$(CH_2)_nO(CH_2)_nOH$, —CHO or a 5-or 6 membered heterocyclic group that is optionally bonded via an alkylene group.
$R^5$ and $R^{5'}$ are each independently hydrogen or lower alkyl or together with the carbon atom to which they are attached form a cycloalkyl group;
$R^6$ and $R^{6'}$ are each independently hydrogen, halogen, trifluoromethyl, lower alkoxy or cyano; or
$R^6$ and $R^{6'}$ together form —CH=CH—CH=CH—, which is optionally substituted by one or two substituents selected from lower alkyl or lower alkoxy;
X is —$C(O)N(R^3)$—, —$(CH_2)_mO$—, —$(CH_2)_mN(R^3)$—, —$N(R^3)C(O)$—, or —$N(R^3)(CH_2)_m$—;
n is 0-4; and
m is 1 or 2.

Compounds of formula II are described in EP-A-1035115, such as

N-(3,5-Bis-trifluoromethyl-benzyl)-N-methyl-6-[methyl-(2-morpholin-4-yl-ethyl)-amino]-4-o-tolyl-nicotinamide, N-(3,5-Bis-trifluoromethyl-benzyl)-N-methyl-6-morpholin-4-yl-4-o-tolyl-nicotinamide, N-(3,5-Bis-trifluoromethyl-benzyl)-N-methyl-6-thiomorpholin-4-yl-4-o-tolyl-nicotinamide, N-(3,5-Bis-trifluoromethyl-benzyl)-N-methyl-6-(1-oxo-$1\lambda^6$-4-thiomorpholin-4-yl)-4-o-tolyl-nicotinamide, N-(3,5-Bis-trifluoromethyl-benzyl)-6-(1,1-dioxo-$1\lambda^6$-6-thiomorpholin-4-yl)-N-methyl-4-o-tolyl-nicotinamide, N-(3,5-Bis-trifluoromethyl-benzyl)-N-methyl-6-piperazin-1-yl-4-o-tolyl-nicotinamide, N-(3,5-Bis-trifluoromethyl-benzyl)-6-[4-(2-hydroxy-ethyl)-piperazin-1-yl]-N-methyl-4-o-tolyl-nicotinamide, 2-(3,5-bis-trifluoromethyl-phenyl)-N-[6-(4-methyl-piperazin-1-yl)-4-o-tolyl-pyridin-3-yl]-N-methyl-isobutyramide, 2-(3,5-bis-trifluoromethyl-phenyl)-N-(6-morpholin-4-yl-4-o-tolyl-pyridin-3-yl)-N-methyl-isobutyramide, 2-(3,5-Bis-trifluoromethyl-phenyl)-N-[4-(4-fluoro-2-methyl-phenyl)-6-(4-methyl-piperazin-1-yl)-pyridin-3-yl]-N-methyl-isobutyramide, 2-(3,5-Bis-trifluoromethyl-phenyl)-N-[4-(2-chloro-phenyl)-pyridin-3-yl]-N-methyl-isobutyramide, 2-(3,5-Bis-trifluoromethyl-phenyl-N-methyl-N-(4-o-tolyl-pyridin-3-yl)-isobutyramide, 2-(3,5-Bis-trifluoromethyl-phenyl)-N-methyl-N-[6-(4-pyrimidin-2-yl-piperazin-1-yl)-4—o—tolyl-pyridin-3-yl]-isobutyramide, 2-(3,5-Bis-trifluoromethyl-phenyl)-N-(6-morpholin-4-yl-4-o-tolyl-pyridin-3-yl)-isobutyramide, 2-(3,5-Bis-trifluoromethyl-phenyl)-N-[4-(2-chloro-phenyl)-6-dimethylamino-pyridin-3-yl]-isobutyramide, 2-(3,5-Bis-trifluoromethyl-phenyl)-N-methyl-N-(6-piperazin-1-yl-4-o-tolyl-pyridin-3-yl)-isobutyramide, and 2-(3,5-bis-trifluoromethyl-phenyl)-N-[6-(1,1-dioxo-$1\lambda^6$-thiomorpholin-4-yl)-4-o-tolyl-pyridin-3-yl]-N-methyl-isobutyramide.

These compounds of formula II are antagonists of the Neurokinin 1 (NK-1, substance P) receptor. The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease. Furthermore, these compounds are useful in the treatment of pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases. Furthermore, the compounds may be useful in the treatment of a number of physiological disorders, which include disorders of the central nervous system such as anxiety, depression and psychosis. The neurokinin-1 receptor antagonists are further useful for the treatment of motion sickness, for treatment induced vomiting and for the reduction of cisplatin-induced emesis.

The compounds of formula II can be manufactured according to e.g. EP-A-1035115. In one such method of manufacture, compounds of formula II are prepared from compounds of formula I.

Compounds of formula I

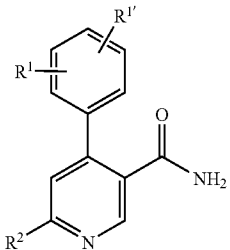

I wherein

R¹ and R¹' are each independently hydrogen, lower alkyl, lower alkoxy, halogen, cyano or alkylamino;

R² is —N(R³)₂, —N(R³)(CH₂)ₙOH, —N(R³)S(O)₂-lower alkyl, —N(R³)S(O)₂-phenyl,-N═CH—N(R³)₂, —N(R³)C(O)R³ or a cyclic tertiary amine of the formula

 or the group

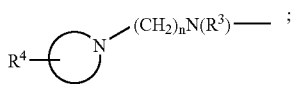

each R³ is independently from each other, hydrogen, C₃₋₆-cycloalkyl, benzyl or lower alkyl;

R⁴ is hydrogen, hydroxy, lower alkyl, —(CH₂)ₙCOO-lower alkyl, —N(R³)CO-lower alkyl, hydroxy-lower alkyl, cyano, —(CH₂)ₙO(CH₂)ₙOH, —CHO or a 5-or 6-membered heterocyclic group that is optionally bonded via an alkylene group are valuable intermediate products for the manufacture of therapeutically active compounds of formula II.

It is known (EP-A-1035115) that the present compounds of formula I can be prepared for example, by processes described in scheme 1 below:

Scheme 1

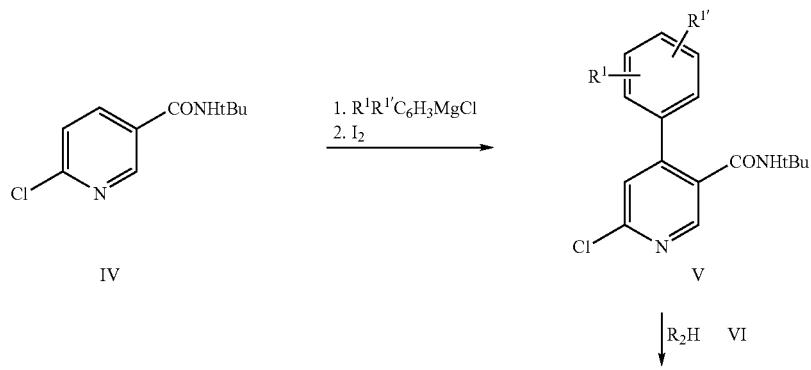

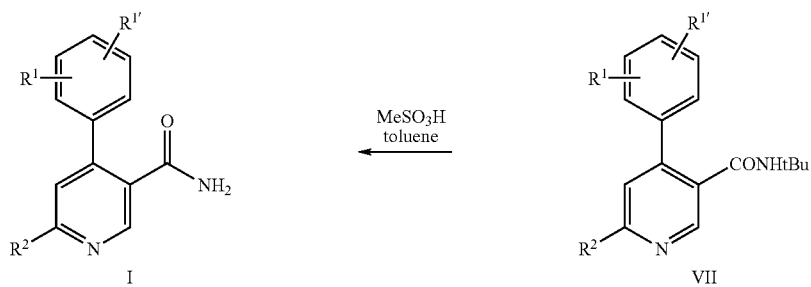

This method for manufacturing the compounds of formula I is high-yielding but requires the use of expensive starting materials. Furthermore, the key step in this method is the substitution of the pyridine with $R^1R^{1'}C_6H_3MgCl$ by Grignard Reaction. The success of this reaction depends on the substitution pattern on the aromatic ring. In case that electron withdrawing groups decrease the reactivity of the Grignard reagent, a Suzuki type reaction (Suzuki Coupling) must be performed.

The problem at the root of the present invention is therefore to provide a process for preparing the compounds of formula I, which process is preferred in case the Grignard Reaction will not work or does not work well.

SUMMARY OF THE INVENTION

The present invention relates to a process for the manufacture of compounds of formula

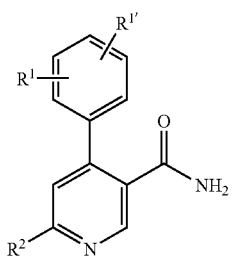

I wherein $R^1$ and $R^{1'}$ are each independently hydrogen, lower alkyl, lower alkoxy, halogen, cyano or alkylamino;

$R^2$ is —$N(R^3)_2$, —$N(R^3)(CH_2)_nOH$, —$N(R^3)S(O)_2$-lower alkyl, —$N(R^3)S(O)_2$-phenyl, —N=CH—$N(R^3)_2$, —$N(R^3)C(O)R^3$ or a cyclic tertiary amine of the formula

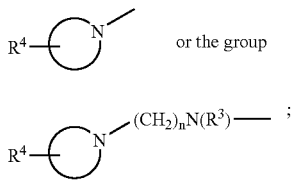

each $R^3$ is independently hydrogen, $C_{3-6}$-cycloalkyl, benzyl or lower alkyl;

$R^4$ is hydrogen, hydroxy, lower alkyl, —$(CH_2)_n$COO-lower alkyl, —$N(R^3)$CO-lower alkyl, hydroxy-lower alkyl, cyano, —$(CH_2)_nO(CH_2)_nOH$, —CHO or a 5-or 6-membered heterocyclic group which is optionally bonded via an alkylene group.

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain alkyl group containing from 1-7 carbon atoms, for example, methyl, ethyl, propyl, isopropyl, n-butyl, i-butyl, t-butyl and the like. Preferred lower alkyl groups are groups with 1-4 carbon atoms.

The term "lower alkoxy" denotes a group wherein the alkyl residues are as defined above, and which is attached via an oxygen atom.

The term "halogen" denotes chlorine, iodine, fluorine and bromine.

The term "cycloalkyl" denotes a saturated carbocyclic group, containing 3-6 carbon atoms.

The term "cyclic tertiary amine" denotes, for example, pyrrol-1-yl, imidazol-1-yl, piperidin-1-yl, piperazin-1-yl, morpholin-4-yl, thiomorpholin-4-yl, 1-oxo-thiomorpholin-4-yl or 1,1-dioxo-thiomorpholin-4-yl.

The term "5 or 6 membered heterocyclic group" denotes, for example pyridinyl, pyrimidinyl, oxadiazolyl, triazolyl, tetrazolyl, thiazolyl, thienyl, furyl, pyranyl, pyrrolyl, imidazolyl, pyrazolyl, isothiazolyl, piperazinyl or piperidyl.

The problem exhibited by the prior art process is solved, according to the present invention, by a process for preparing the compounds of formula I as show in scheme 2:

Scheme 2

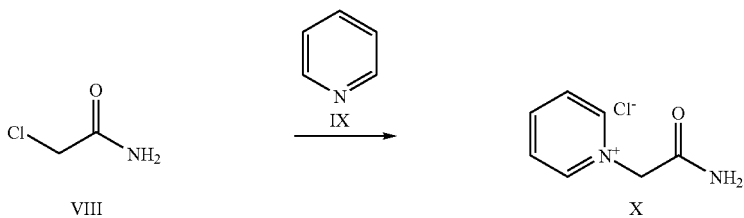

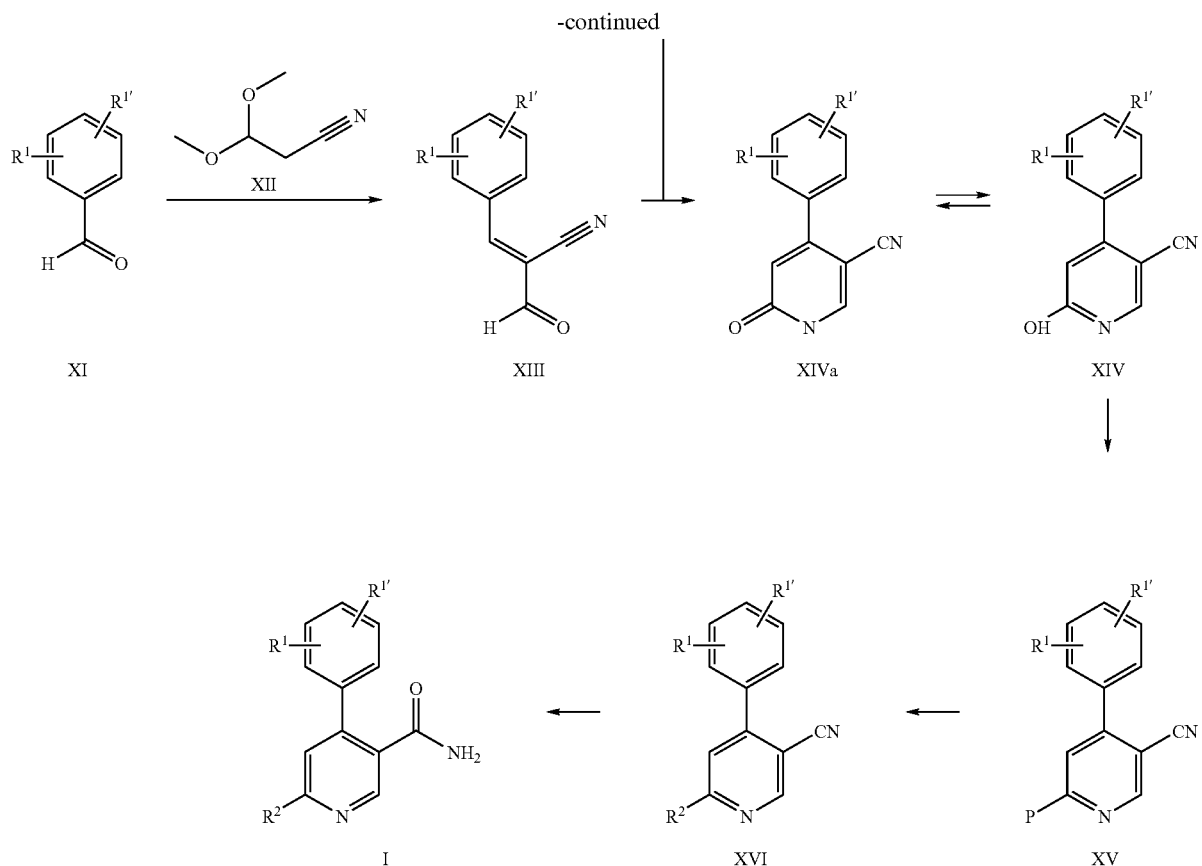

In scheme 2 the definition of substituents for $R^1$, $R^{1'}$ and $R^2$ is described above.

The compound of formula

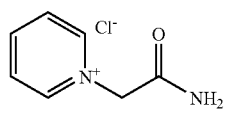

is obtained in good yield by the reaction of 2-chloroacetamide with pyridine. The reaction is described in A. R. Katritzky, N. E. Grzeskowiak and J. Alvarez-Builla, J. C. S. Perkin I, 1981, 1180-1185.

The preparation of compound of formula XIII

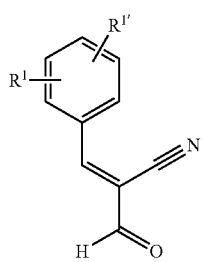

consists of two steps:

Step 1)

A solution of 3,3-dimethoxypropionitrile (XII) and compound of formula XI is added to sodium methanolate in an alcohol, such as lower alkyl alcohol or cycloalkyl alcohol, preferably methanol by keeping the internal temperature below 30° C., preferably below 20° C. The reaction mixture is stirred at a temperature varying between 20-30° C., preferably between 22-25° C., for 5 to 20 hours, preferably 10 to 12 hours.

Step 2)

An acid, for example, acetic acid, $H_2SO_4$ or HCl is then added to the reaction mixture at a temperature between 10-30° C., preferably between 15-25° C. After stirring the resulting mixture for 5 to 180 minutes, preferably 30 to 60 minutes, the compound of formula XIII is obtained in good yield.

The process according to the present invention for preparing the compounds of formula I comprising the steps of:

a) reacting a compound of formula X

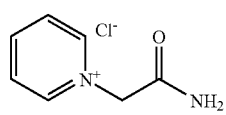

with a compound of formula

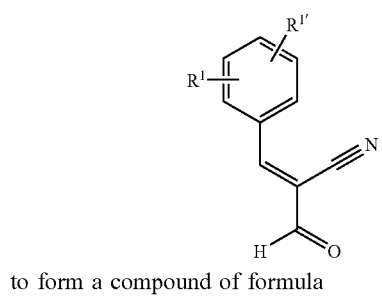

XIII to form a compound of formula

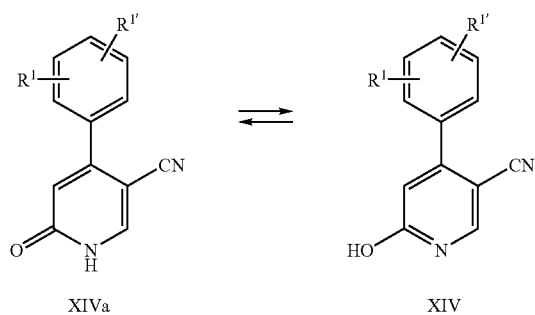

XIVa     XIV wherein the definition of substituents are described above.

A more detailed description of step a) follows:

Step a1)

The reaction takes place in an organic solvent, such as ether, ketone or alcohol, preferably alcohol, most preferably methanol. The reaction mixture is treated with an organic base, such as triethylamine at about 10 to 50° C., preferably 20 to 30° C. The reaction mixture is stirred for 0.5 to 12 hours, preferably 2 hours, and concentrated in vacuum.

Step a2)

The residue is then taken up in an organic solvent, such as dichloromethane, treated with (chloromethylene)dimethylammonium chloride (Vilsmeiers Reagent) and heated to 30 to 60° C., preferably 45° C., for 0.5 to 5 hours, preferably 1 hour. In order to remove all volatile matter, the mixture is concentrated in vacuum.

Step a3)

The resulting residue is heated neat or dissolved in a solvent having a high boiling temperature, such as xylene, toluene or diphenylether, to 150 to 240° C., preferably 170 to 200° C., most preferably 180-190° C., for 10 to 60 minutes, preferably 15 minutes, and then cooled down to 10 to 30° C., preferably 20-25° C., and dissolved in an organic solvent and purified by extraction with water. The layers are separated. Evaporation of the organic phase in a vacuum gives a product of formula

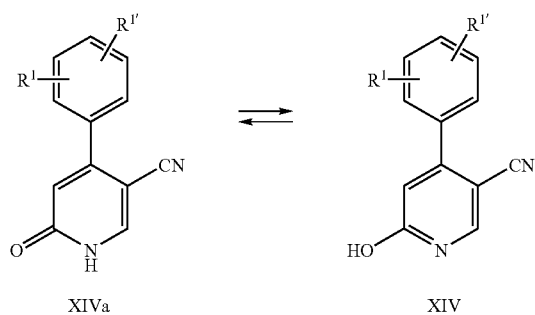

XIVa     XIV b) converting the OH/=O function of compounds of formula XIV/XIVa into a leaving group P

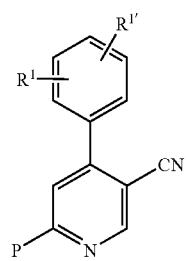

XV wherein P is halogen or —O—SO$_2$CF$_3$.

The reaction of compound of formula XIV with reagents containing leaving groups, for example, POCl$_3$, PBr$_3$, MeI or (F$_3$CSO$_2$)$_2$O, is carried out in an organic solvent, for example dichloromethane, trifluoromethyl benzene or chlorobenzene and at a temperature of about 40 to 80° C., preferably about 50° C., for 60 to 240 minutes, preferably 80 minutes.

c) substituting the leaving group P of formula XV with the group R$^2$ by reacting the compound of formula XV with HR$^2$ to form a compound of formula

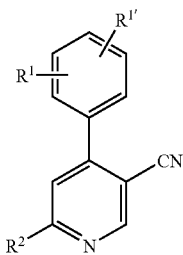

XVI wherein the definition of substituents for R$^1$, R$^{1'}$ and R$^2$ is described above.

Step c) is preferably performed in an organic solvent, for example DMF, DMSO, N-methylpyrrolidene chlorobenzene, toluene or mixtures thereof at a temperature of about 60 to 150° C., preferably 90 to 120° C., most preferably 112° C., for 10 to 240 minute, preferably 20 to 120 minute, most preferably 30 to 60 minutes. The mixture is cooled down and treated with an acid, such as sulfuric acid, acetic acid or hydrochloride.

d) hydrolyzing the nitrile function of formula XVI to form a compound of formula

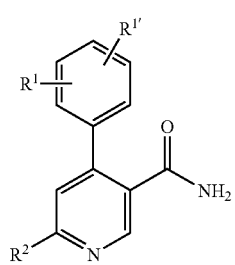

I

Step d) is carried out in an acidic medium, for example H2SO4, HCl or acetic acid, with or without an organic solvent at a temperature of 50 to 140° C., preferably 60 to 90° C., most preferably 70° C., for 1 to 8 hours, preferably 2 hours.

According to a preferred embodiment of the invention, $R^1$ and $R^{1'}$ are each independently hydrogen, lower alkyl, alkoxy, halogen, cyano or alkylamino; P is halogen; and $R^2$ is a cyclic tertiary amine of the formula

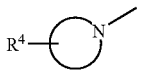

wherein $R^4$ is described above.

According to a more preferred embodiment of the invention, $R^1$ and $R^{1'}$ are each independently hydrogen, lower alkyl, alkoxy, halogen, cyano or alkylamino; P is chloro; and $R^2$ is morpholin-4-yl, 4-methyl-piperazin-1-yl or 1,1,-dioxothiomorpholin-4-yl.

According to a still more preferred embodiment of the invention, the present process is applied for the manufacture of
6-hydroxy-4-o-tolyl-nicotinonitrile,
6-oxo-4-p-tolyl-1,6-dihydro-pyridine-3-carbonitrile,
4-(2-chloro-phenyl)-6-oxo-1,6-dihydro-pyridine-3-carbonitrile,
4-(4-chloro-phenyl)-6-oxo-1,6-dihydro-pyridine-3-carbonitrile,
4-(3-cyano-phenyl)-6-oxo-1,6-dihydro-pyridine-3-carbonitrile,
4-(4-cyano-phenyl)-6-oxo-1,6-dihydro-pyridine-3-carbonitrile,
4-(4-methoxy-phenyl)-6-oxo-1,6-dihydro-pyridine-3-carbonitrile,
4-(3-methoxy-phenyl)-6-oxo-1,6-dihydro-pyridine-3-carbonitrile,
4-(2-methoxy-phenyl)-6-oxo-1,6-dihydro-pyridine-3-carbonitrile,
4-(4-dimethylamino-phenyl)-6-oxo-1,6-dihydro-pyridine-3-carbonitrile,
6-oxo-4-phenyl-1,6-dihydro-pyridine-3-carbonitrile,
N-(6-oxo-4-phenyl-1,6-dihydro-pyridine-3-yl)-acetamide,
6-chloro-4-o-tolyl-nicotinonitrile,
6-morpholin-4-yl-4-tolyl-nicotinonitrile,
6-(4-methyl-piperazin-1-yl)-4-o-tolyl-nicotinonitrile,
6-(1,1-dioxo-1$\lambda^6$-6-thiomorpholin-4-yl)-tolyl-nicotinonitrile,
6-morpholin-4-yl-4-o-tolyl-nicotinamide,
6-(4-methylpiperazin-1-yl)-4-o-tolyl-nicotinamide, and
6-(1,1-dioxo-1$\lambda^6$-6-thiomorpholin-4-yl)-tolyl-nicotinamide.

Preferred embodiments of the present invention are described in more detail by following examples 1 to 14.

EXAMPLE 1

6-Morpholin-4-yl-4-o-tolyl-nicotinamide a) 1-Carbamoylmethyl-pyridinium Chloride 50.00 g (524.01 mmol) 2-chloroacetamide were suspended in 100 ml acetonitrile. 41.45 g (524.01 mmol) pyridine were added, and the suspension was heated at 90° C. for 10 hours. The suspension was cooled to 22° C., suction filtered and washed with 100 ml hexane. The product 1-carbamoylmethyl-pyridinium chloride (79.10 g) was obtained as colorless crystals after being recrystallized from ethanol, m.p 205.2° C.

$H^1$ NMR (400 MHz, CDCl$_3$, ppm). 5.50 (s, 2H), 7.72 (s, 1H), 8.17-8.20 (m, 2H), 8.32 (s, 1H), 8.64-8.68 (m, 1H), 9.04 (d, 2H).

b) 2-Formyl-3-o-tolyl-acrylonitrile

A solution of 13.19 g (110.00 mmol) 3,3-dimethoxypropionitrile and 12.39 g (100.00 mmol) o-tolylaldehyde was added to 23.40 g (130.00 mmol) sodium methanolate in 22.0 ml methanol by keeping the internal temperature below 20° C. The reaction mixture was stirred at 22-25° C. overnight and concentrated in vacuo (rotary evaporator at 40° C. and 20 mbar). 100.00 ml HCl (25%) were added at 15-25° C. and the resulting mixture stirred for 60 minutes. The precipitate was suction filtered, washed with 30 ml methanol (precooled to −20° C.) and dried in vacuo to afford 16.14 g of 2-formyl-3-o-tolyl-acrylonitrile as yellowish crystals, m.p. 81.5° C.

$H^1$ NMR (300 MHz, DMSO, ppm). 2.51 (s, 1H), 7.41-7.58 (m, 3H), 8.06 (d, 1H), 8.76 (s, 1H), 9.74 (s, 1H). MS (EI): m/e=171([M] 30), 156 (100), 143 (23), 115 (46).

c) 6-Hydroxy-4-o-tolyl-nicotinonitrile 1.726 g (10.0 mmol) 1-carbamoylmethyl-pyridinium chloride and 1.712 g (10.0 mmol) 2-formyl-3-o-tolyl-acrylonitrile in 24.8 ml methanol were treated with 1.05 g (10.4 mmol) triethylamine at 20-30° C. The reaction mixture was stirred for 2 hours and concentrated in vacuo (rotary evaporator at 40° C. and 20 mbar). The residue was taken up in 50 ml dichloromethane, treated with 2.56 g (20.0 mmol) (chloromethylene)dimethylammonium chloride (Vilsmeiers Reagent) and heated at 45° C. for 1 hour. In order to remove all volatile matter, the mixture was concentrated in vacuo (rotary evaporator at 45° C. and 20 mbar). The residue was heated to 180-190° C. for 15 minutes, cooled down to 20-25° C. and distributed in 80.0 ml dichloromethane and 80.0 ml water. The layers were separated. Evaporation of the organic phase in vacuo gave 1.37 g of amorphous product of 6-hydroxy-4-o-tolyl-nicotinonitrile.

$H^1$ NMR (400 MHz, CDCl$_3$, ppm). 2.30 (s, 3H), 6.54 (s, 1H), 7.18 (d, 1H), 7.28-7.38 (m, 3H), 7.92 (s, 1H). NH ? MS (ISP): 211 ([M+H$^+$] 100).

d) 6-Chloro-4-o-tolyl-nicotinonitrile

A mixture of 2.5 g (11.89 mmol) 6-hydroxy-4-o-tolyl-nicotinonitrile, 3.64 g (23.78 mmol) phosphorus oxychloride in 10.0 ml dichloromethane was heated at 50° C. for 80 minutes. The mixture was cooled down to 20-25° C., poured on water by keeping the internal temperature between 20-30° C. and extracted by adding additional 80.0 ml dichloromethane. Evaporation of the organic phase in vacuo gave 2.9 g of crude product of 6-chloro-4-o-tolyl-nicotinonitrile which was purified by chromatography over silica gel (ethylacetate:hexane=4:1) to afford 2.4 g of, m.p. 112.4° C.

$H^1$ NMR (400 MHz, CDCl$_3$, ppm). 2.24 (s, 3H), 7.16 (s, 1H), 7.30-7.41 (m, 4H), 8.74 (s, 1H). MS (ISP): 229 ([M+H$^+$] 100).

e) 6-Morpholin-4-yl-4-tolyl-nicotinonitrile 500 mg (2.1865 mmol) 6-chloro-4-o-tolyl-nicotinonitrile were dissolved in 10.0 ml toluene and heated to 112° C. At this temperature 762 mg (8.746 mmol) morpholine were added and the reaction mixture was stirred for a further 30 minutes. The mixture was cooled down to 20-25° C. and treated with 900 mg sulfuric acid (95%). The organic phase was washed with 5 ml water (pH of the water phase 7-7.5). Evaporation in vacuo gave 530 mg of 6-morpholin-4-yl-4-tolyl-nicotinonitrile as a white foam.

H$^1$ NMR (300 MHz, CDCl$_3$, ppm). 2.24 (s, 3H), 3.65-3.68 (m, 4H), 3.77-3.82 (m, 4H), 6.47 (s, 1H), 7.15-7.35 (m, 4H), 8.48 (s, 1H). MS (ISP): 280 ([M+H$^+$] 100).

f) 6-Morpholin-4-yl-4-o-tolyl-nicotinamide

A mixture of 500 mg (1.79 mmol) crude 6-morpholin-4-yl-4-tolyl-nicotinonitrile, 0.5 ml toluene and 475 mg sulfuric acid (95%) were heated at 70° C. for 2 hours. The suspension was cooled down to 20-25° C. and quenched with 5 ml water. 5 ml ethylacetate were added followed by a solution of 710 mg sodium hydroxide in 2 ml water. Evaporation of the organic phase in vacuo gave 700 mg colorless solid. After purification by chromatography over silica gel (ethyl acetate/hexane 1:2) 490 mg of 6-morpholin-4-yl-4-o-tolyl-nicotinamide were obtained as colorless crystals, m.p. 144-145° C.

H$^1$ NMR (300 MHz, CDCl$_3$, ppm). 2.15 (s, 3H), 3.62-3.64 (m, 4H), 3.80-3.82 (m, 4H), 5.0-5.3 (br, 2H), 6.30 (s, 1H), 7.2-7.37 (m, 4H), 8.94 (s, 1H). MS (EI): m/e=297 ([M] 64), 266 ([M-CH$_2$OH] 100).

EXAMPLE 2

6-(4-Methyl-piperazin-1-yl)-4-o-tolyl-nicotinamide a) 6-(4-Methyl-piperazin-1-yl)-4-o-tolyl-nicotinonitrile:

500 mg (2.1865 mmol) 6-chloro-4-o-tolyl-nicotinonitrile were dissolved in 10.0 ml toluene and heated to 112° C. At this temperature 2.19 g (21.865 mmol) 1-methylpiperazine were added, and the reaction mixture was stirred for further 60 minutes. The mixture was cooled down to 50° C. and concentrated under reduced pressure. 5 ml toluene were added to the obtained residue at a temperature of 20-25° C., followed by 900 mg sulfuric acid (95%). The organic phase was washed with 5 ml water. Evaporation in vacuo gave 520 mg of 6-(4-methyl-piperazin-1-yl)-4-o-tolyl-nicotinonitrile as a beige foam.

H$^1$ NMR (300 MHz, CDCl$_3$, ppm). 2.25 (s, 3H), 2.35 (s, 3H), 2.46-2.52 (m, 4H), 3.70-3.73 (m, 4H), 6.48 (s, 1H), 7.15-7.37 (m, 4H), 8.46 (s, 1H). MS (ISP): 293 ([M+H$^+$] 100).

b) 6-(4-Methyl-piperazin-1-yl)-4-o-tolyl-nicotinamide 480 mg (1.642 mmol) 6-(4-methyl-piperazin-1-yl)-4-o-tolyl-nicotinonitrile were treated with 3.8 ml sulfuric acid (90%) and heated at 80° C. for 1 hour. The mixture was cooled down to 20-25° C. and treated with 20 ml ethyl acetate. 2.0 g sodium hydroxide solution (28%) was added and the organic phase was washed with 6 ml water. Evaporation in vacuo gave 380 mg of 6-(4-methylpiperazin-1-yl)-4-o-tolyl-nicotinamide as a light yellow crystalline foam.

H$^1$ NMR (400 MHz, CDCl$_3$, ppm). 2.15 (s, 3H), 2.34 (s, 3H), 2.45-2.52 (m, 4H), 3.67-3.73 (m, 4H), 5.01-5.28 (b, 2H), 6.31 (s, 1H), 7.20-7.36 (m, 4H), 8.93 (s, 1H). MS (ISP): 332 ([M+H$^+$] 100).

EXAMPLE 3

6-(1,1-Dioxo-1$\lambda^6$-6-thiomorpholin-4-yl)-tolyl-nicotinamide a) 6-(1,1-Dioxo-1$\lambda^6$-6-thiomorpholin-4-yl)-tolyl-nicotinonitrile A mixture of 500 mg (2.1865 mmol) 6-chloro-4-o-tolyl-nicotinonitrile, 1.478 g (10.9325 mmol) thiomorpholin 1,1-dioxide and 5 ml ethyl acetate were heated at 80° C. for 12 hours. The mixture was cooled down to 20-25° C. and treated with 7.5 ml ethyl acetate, followed by 5.0 ml water. The organic phase was washed with 5.0 ml water and concentrated under reduced pressure. Crystallization from dichloromethane/hexane 1:2 gave 450 mg of 6-(1,1-dioxo-1$\lambda^6$-6-thiomorpholin-4-yl)-tolyl-nicotinonitrile as beige crystals, m.p. 182.7° C.

H$^1$ NMR (300 MHz CDCl$_3$, ppm). 2.24 (s, 3H), 3.07-3.11 (m, 4H), 4.24-4.28 (m,4H), 6.63 (s, 1H), 7.14-7.41 (m, 4H), 8.52 (s, 1H). MS (ISP): 328 ([M+H$^+$] 100).

b) 6-(1,1-dioxo-1$\lambda^6$-6-thiomorpholin-4-yl)-tolyl-nicotinamide 400 mg (1.222 mmol) 6-(1,1-dioxo-1$\lambda^6$-6-thiomorpholin-4-yl)-tolyl-nicotinonitrile were diluted with 400 mg sulfuric acid (95%) and heated at 70° C. for 2 hours. The mixture was cooled down to 20-25° C. and treated with 5 ml ethyl acetate, followed by a solution of 600 mg sodium hydroxide in 2 ml water. The organic phase was washed twice with 2 ml water and concentrated under reduced pressure to yield 360 mg of 6-(1,1-dioxo-1$\lambda^6$-6-thiomorpholin-4-yl)-tolyl-nicotinamide as white crystals, m.p. 239.7° C.

H$^1$ NMR (300 MHz, DMSO, ppm). 2.11 (s, 1H), 3.07-3.18 (m, 4H), 4.06-4.17 (m, 4H), 6.77 (s, 1H), 7.06-7.26 (m, 6H), 8.40 (s, 1H). MS (ISP): 346 ([M+H$^+$] 100).

EXAMPLE 4

6-Oxo-4-p-tolyl-1,6-dihydro-pyridine-3-carbonitrile

The synthesis was performed analogous to example 1c using 1-carbamoylmethyl-pyridinium chloride and 2-propenenitrile, 2-formyl-3-p-tolyl to produce 6-oxo-4-p-tolyl-1,6-dihydro-pyridine-3-carbonitrile (amorphous).

H$^1$ NMR (400 MHz, DMSO, ppm). 2.37 (s, 3H), 6.40 (s, 1H), 7.33 (d, 2H), 7.45 (d, 2H), 8.35 (s, 1H), 12.71 (s, 1H). MS (EI): m/e=210 ([M] 15), 86 (100), 58 (30).

2-Propenenitrile, 2-formyl-3-p-tolyl was synthesized analogous to example 1b using 3,3-Dimethoxypropionitrile and p-tolylaldehyde.

EXAMPLE 5

4-(2-Chloro-phenyl)-6-oxo-1,6-dihydro-pyridine-3-carbonitrile

The synthesis was performed analogous to example 1c using 1-carbamoylmethyl-pyridinium chloride and 2-propenenitrile, 2-formyl-3-(2-chloro-phenyl) to produce 4-(2-chloro-phenyl)-6-oxo-1,6-dihydro-pyridine-3-carbonitrile (amorphous).

H$^1$ NMR (400 MHz, CDCl$_3$, ppm). 6.59 (s, 1H), 7.26-7.55 (m, 5H), 7.92 (s, 1H). MS (ISP): 231 ([M+H$^+$] 100).

2-Propenenitrile, 2-formyl-3-(2-chloro-phenyl) was synthesized analogous to example 1b using 3,3-dimethoxypropionitrile and o-chloro-benzaldehyde.

EXAMPLE 6

4-(4-Chloro-phenyl)-6-oxo-1,6-dihydro-pyridine-3-carbonitrile

The synthesis was performed analogous to example 1c using 1-carbamoylmethyl-pyridinium chloride and 2-propenenitrile, 2-formyl-3-(4-chloro-phenyl) to produce 4-(4-chloro-phenyl)-6-oxo-1,6-dihydro-pyridine-3-carbonitrile.

$H^1$ NMR (400 MHz, DMSO, ppm). 6.46 (s, 1H), 7.59 (s, 4H), 8.38 (s, 1H), 12.81 (s, 1H). MS (ISP): 231 ([M+H$^+$] 100).

2-Propenenitrile, 2-formyl-3-(4-chloro-phenyl) was synthesized analogous to example 1b using 3,3-dimethoxypropionitrile and o-chloro-benzaldehyde.

EXAMPLE 7

4-(3-cyano-phenyl)-6-oxo-1,6-dihydro-pyridine-3-carbonitrile

The synthesis was performed analogous to example 1c using 1-carbamoylmethyl-pyridinium chloride and 2-propenenitrile, 2-formyl-3-(3-cyano-phenyl) to produce 4-(3-cyano-phenyl)-6-oxo-1,6-dihydro-pyridine-3-carbonitrile (amorphous).

$H^1$ NMR (400 MHz, DMSO, ppm). 6.55 (s, 1H), 7.74 (t, 1H), 7.91 (d, 1H), 7.99 (d, 1H), 8.06 (s, 1H), 8.42 (s, 1H), 12.72 (s, 1H). MS (ISN): 220 ([M−H] 100).

2-Propenenitrile, 2-formyl-3-(3-cyano-phenyl) was synthesized analogous to example 1b using 3,3-Dimethoxypropionitrile and m-cyano-benzaldehyde.

EXAMPLE 8

4-(4-Cyano-phenyl)-6-oxo-1,6-dihydro-pyridine-3-carbonitrile

The synthesis was performed analogous to example 1c using 1-carbamoylmethyl-pyridinium chloride and 2-propenenitrile, 2-formyl-3-(4-cyano-phenyl) to produce 4-(4-cyano-phenyl)-6-oxo-1,6-dihydro-pyridine-3-carbonitrile (amorphous).

$H^1$ NMR (400 MHz, DMSO, ppm). 6.52 (s, 1H), 7.76 (d, 2H), 8.01 (d, 2H), 8.42 (s, 1H), 12.87 (s, 1H). MS (ISN): 220 ([M−H] 100).

2-Propenenitrile, 2-formyl-3-(4-cyano-phenyl) was synthesized analogous to example 1b using 3,3-dimethoxypropionitrile and p-cyano-benzaldehyde.

EXAMPLE 9

4-(4-Methoxy-phenyl)-6-oxo-1,6-dihydro-pyridine-3-carbonitrile

The synthesis was performed analogous to example 1c using 1-carbamoylmethyl-pyridinium chloride and 2-propenenitrile, 2-formyl-3-(4-methoxy-phenyl) to produce 4-(4-methoxy-phenyl)-6-oxo-1,6-dihydro-pyridine-3-carbonitrile (amorphous). $H^1$ NMR (400 MHz, DMSO, ppm). 3.82 (s, 3H), 6.33 (s, 1H), 7.06 (d, 2H), 7.51 (d, 2H), 8.31 (s, 1H), 12.54 (s, 1H). MS (ISN): m/e=226 (32), 225 (M−H, 100).

2-Propenenitrile, 2-formyl-3-(4-methoxy-phenyl) was synthesized analogous to example 1b using 3,3-Dimethoxypropionitrile and p-methoxy-benzaldehyde.

EXAMPLE 10

4-(3-Methoxy-phenyl)-6-oxo-1,6-dihydro-pyridine-3-carbonitrile

The synthesis was performed analogous to example 1c using 1-carbamoylmethyl-pyridinium chloride and 2-propenenitrile, 2-formyl-3-(3-methoxy-phenyl) to produce 4-(3-methoxy-phenyl)-6-oxo-1,6-dihydro-pyridine-3-carbonitrile (amorphous).

$H^1$ NMR (400 MHz, CDCl$_3$, ppm). 3.87 (s, 3H), 6.66 (s, 1H), 7.04-7.07 (m, 2H), 7.12-7.41 (m, 3H), 7.94 (s, 1H). MS (ISP): 227 ([M+H+] 100).

2-Propenenitrile, 2-formyl-3-(3-methoxy-phenyl) was synthesized analogous to example 1b using 3,3-dimethoxypropionitrile and m-methoxy-benzaldehyde.

EXAMPLE 11

4-(2-Methoxy-phenyl)-6-oxo-1,6-dihydro-pyridine-3-carbonitrile

The synthesis was performed analogous to example 1c using 1-carbamoylmethyl-pyridinium chloride and 2-propenenitrile, 2-formyl-3-(2-methoxy-phenyl) to produce 4-(2-methoxy-phenyl)-6-oxo-1,6-dihydro-pyridine-3-carbonitrile (amorphous).

$H^1$ NMR (400 MHz, CDCl$_3$, ppm). 3.89 (s, 3H), 6.59 (s, 1H), 7.02-7.46 (m, 4H), 7.84 (s, 1H), 12.91 (s, 1H). MS (ISP): 227 ([M+H$^+$] 100).

2-Propenenitrile, 2-formyl-3-(2-methoxy-phenyl) was synthesized analogous to example 1b using 3,3-dimethoxypropionitrile and o-methoxy-benzaldehyde.

EXAMPLE 12

4-(4-Dimethylamino-phenyl)-6-oxo-1,6-dihydro-pyridine-3-carbonitrile

The synthesis was performed analogous to example 1c using 1-carbamoylmethyl-pyridinium chloride and 2-propenenitrile, 2-formyl-3-(4-dimethylamino-phenyl) to produce 4-(4-dimethylamino-phenyl)-6-oxo-1,6-dihydro-pyridine-3-carbonitrile (amorphous).

$H^1$ NMR (400 MHz, DMSO, ppm). 2.97 (s, 6H), 6.26 (s, 1H), 6.79 (d, 2H), 7.43 (d, 2H), 8.25 (s, 1H), 9.18 (s, 1H). MS (ISP): 240 ([M+H$^+$] 100), 262 ([M+Na$^+$], 10).

2-Propenenitrile, 2-formyl-3-(4-dimethylamino-phenyl) was synthesized analogous to example 1b using 3,3-dimethoxypropionitrile and p-dimethylamino-benzaldehyde.

EXAMPLE 13

6-Oxo-4-phenyl-1,6-dihydro-pyridine-3-carbonitrile

The synthesis was performed analogous to example 1c using 1-carbamoylmethyl-pyridinium chloride and 2-cyanocinnamic aldehyde to produce 6-oxo-4-phenyl-1,6-dihydro-pyridine-3-carbonitrile (amorphous).

$H^1$ NMR (300 MHz, DMSO, ppm). 6.44 (s, 1H), 7.51-7.58 (m, 5H), 8.39 (s, 1H), 12.60 (s, 1H). MS (ISN): 195 ([M−H] 100).

2-Cyano-cinnamic aldehyde was synthesized analogous to example 1b using 3,3-dimethoxypropionitrile and benzaldehyde.

EXAMPLE 14

N-(6-oxo-4-phenyl-1,6-dihydro-pyridine-3-yl)-acetamide

The synthesis was performed analogous to example 1c using 1-carbamoylmethyl-pyridinium chloride and 2-acetamido-cinnamic aldehyde. In this case treatment with Vilsmeiers Reagent was not required. The obtained residue after Michael Addition Reaction was directly heated at 190° C. for 30 min to produce N-(6-oxo-4-phenyl-1,6-dihydro-pyridine-3-yl)-acetamide (amorphous).

$H^1$ NMR (400 MHz, DMSO, ppm). 1.78 (s, 3H), 6.27 (s, 1H), 7.35-7.43 (m, 6H), 9.01 (s, 1H), 11.5 (s, 1H). MS (ISP): 229 ([M+H$^+$] 100), 187 (15).

2-Acetamido-cinnamic aldehyde was synthesized in analogy to a described procedure (K. Eiter, E. Sackl, *Monatshefte für Chemie* 1952, 123-136).

The invention claimed is:
1. A process for the manufacture of a compound of formula

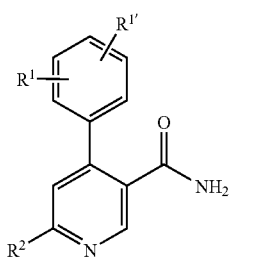

I wherein
  $R^1$ and $R^{1'}$ are each independently hydrogen, lower alkyl, lower alkoxy, halogen, cyano or alkylamino;
  $R^2$ is —N(R$^3$)$_2$, —N(R$^3$)(CH$_2$)$_n$OH, —N(R$^3$)S(O)$_2$-lower alkyl, —N(R$^3$)S(O)$_2$-phenyl, —N=CH—N(R$^3$)$_2$, —N(R$^3$)C(O)R$^3$ or a cyclic tertiary amine of the formula

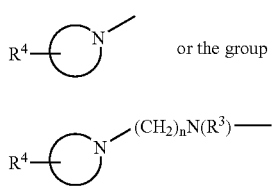

each $R^3$ is independently hydrogen, C$_{3-6}$-cycloalkyl, benzyl or lower alkyl;
  $R^4$ is hydrogen, hydroxy, lower alkyl, —(CH$_2$)$_n$COO-lower alkyl, —N(R$^3$)CO-lower alkyl, hydroxy-lower alkyl, cyano, —(CH$_2$)$_n$O(CH$_2$)$_n$OH, —CHO or a 5-or 6 membered heterocyclic group that is optionally bonded via an alkylene group;
wherein the process comprises the steps of
  a) reacting a compound of formula

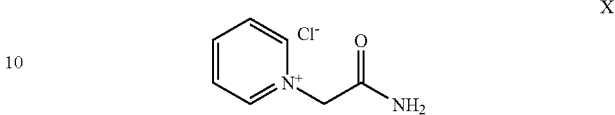

X with a compound of formula

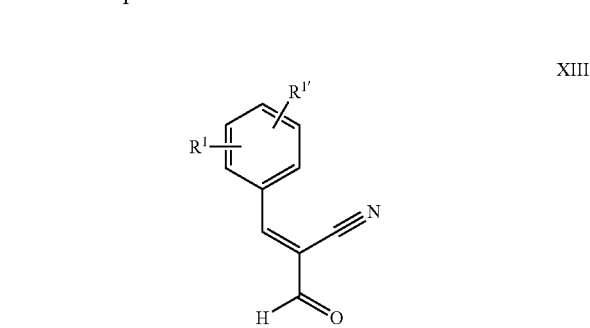

XIII wherein $R^1$ and $R^{1'}$ are as defined above,
to a compound of formula

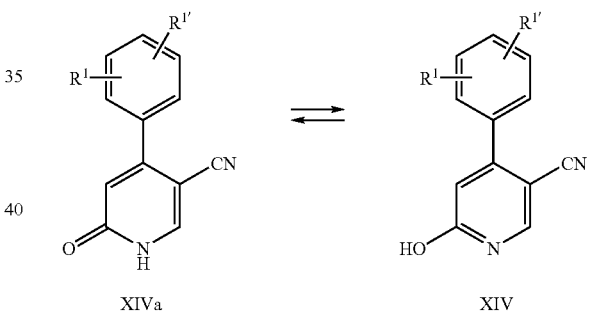

XIVa     XIV wherein the substituents are as defined above;
  b) converting the OH/=O function of compounds of formula XIV/XIVa into a leaving group P with a reagent containing a leaving group selected from the group consisting of POCl$_3$, PBr$_3$, MeI and (F$_3$CSO$_2$)$_2$O to form a compound of formula

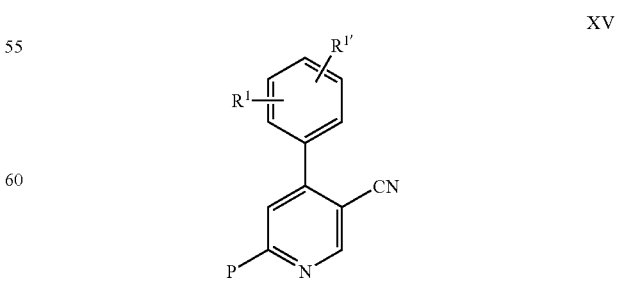

XV wherein P is halogen or trifluoromethanesulfonate and $R^1$ and $R^{1'}$ are as defined above;

c) substituting the leaving group P with the group R² by reacting compound XV with HR² to form a compound of formula

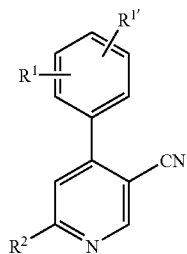

XVI wherein R¹ and R¹' and R² are as defined above; and d) hydrolyzing the nitrile function of compound XVI in an acidic medium comprising $H_2SO_4$, HCl or acetic acid, to form a compound of formula

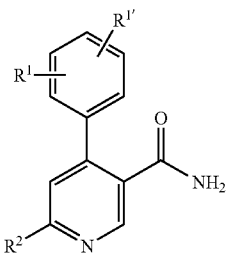

I wherein the definition of the substituents is given above.

2. A process according to claim 1, wherein R¹ and R¹' are each independently hydrogen, lower alkyl, lower alkoxy, halogen, cyano or alkylamino; P is halogen; and R² is a cyclic tertiary amine of the formula

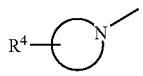

wherein R⁴ is as defined in claim 1.

3. A process according to claim 2, wherein R¹ and R¹' are each independently hydrogen, lower alkyl, lower alkoxy, halogen, cyano or alkylamino; P is chloro; and R² is morpholin-4-yl, 4-methyl-piperazin-1-yl or 1,1-dioxothiomorpholin-4-yl.

4. A process according to claim 1, for the manufacture of 6-morpholin-4-yl-4-o-tolyl-nicotinamide, 6-(4-methylpiperazin-1-yl)-4-o-tolyl-nicotinamide, and 6-(1,1-dioxo-1λ⁶-6-thiomorpholin-4-yl)-tolyl-n icotinamide.

5. A process according to claim 1, wherein the compound of formula XIII is prepared by a process comprising step 1) reacting 3,3-dimethoxypropionitrile (XII) with a compound of formula

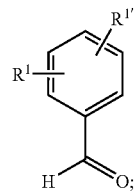

XI and step 2) acidating the reaction mixture formed in step 1).

6. A process according to claim 5, wherein step 1) is carried out in an alcohol at a temperature varying between 20 to 30° C. for 5 to 20 hours.

7. A process according to claim 6, wherein the alcohol is selected from alkyl alcohol and cycloalkyl alcohol.

8. A process according to claim 6, wherein step 1) is carried out in methanol at a temperature varying between 22 to 25° C. for 10 to 12 hours.

9. A process according to claim 5, wherein in step 2) the reaction mixture of step 1) is acidated with an acid selected from acetic acid, $H_2SO_4$ and HCl at a temperature between 10 to 30° C. and with stirring of the resulting mixture for 5 to 180 minutes.

10. A process according to claim 9, wherein the acid is hydrochloride, the temperature is between 15 to 25° C., and the resulting mixture is stirred for 30 to 60 minutes.

11. A process according to claim 1, wherein step a) comprises step a1) reacting compounds of formula X and XII in an organic solvent and treating the reaction mixture with an organic base;

step a2) taking up the reaction mixture obtained in step a1) in an organic solvent and treating the reaction mixture with Vilsmeiers Reagent; and step a3) heating the resulting residue of step a2) neat or dissolved in a solvent having a high boiling temperature.

12. A process according to claim 11, wherein in step a1) the reaction mixture is treated with the organic base triethylamine at a temperature of about 10 to 50° C. with stirring for 0.5 to 12 hours.

13. A process according to claim 12, wherein the organic solvent is selected from ether, ketone and alcohol.

14. A process according to claim 12, wherein step a1) takes place in the organic solvent methanol at a temperature of 20 to 30° C. with stirring for 2 hours.

15. A process according to claim 11, wherein the organic solvent of step a2) is dichloromethane, the Vilsmeiers Reagent is (chloromethylene)dimethylammonium chloride, and the reaction mixture is treated at a reaction temperature of 30 to 60° C. and a reaction time of 0.5 to 5 hours.

16. A process according to claim 15, wherein the reaction temperature is about 45° C. and the reaction time is 1 hour.

17. A process according to claim 11, wherein the solvent of step a3) is xylene, toluene, or diphenylether, and the residue is heated to a temperature of 150 to 240° C. for a reaction time of 10 to 60 minutes.

18. A process according to claim 17, wherein the solvent is toluene, the temperature is about 180-190° C. and the reaction time is 15 minutes.

19. A process according to claim 1, wherein step b) is carried out in an organic solvent at a temperature of about 40 to 80° C. and for a reaction time of 60 to 240 minutes.

20. A process according to claim 19, wherein the organic solvent is selected from dichloromethane, trifluoromethyl benzene and chlorobenzene.

21. A process according to claim 20, wherein the organic solvent is dichloromethane, the temperature is about 50° C. and the reaction time is about 80 minutes.

22. A process according to claim 1, wherein step c) is performed in a solvent selected from DMF, DMSO, N-methylpyrrolidene chlorobenzene, toluene and mixtures thereof at a temperature of about 60 to 150 °C. for a reaction time of 10 to 240 minutes.

23. A process according to claim 22, wherein the solvent is toluene, the temperature is about 112° C. and the reaction time is 30 to 60 minutes.

24. A process according to claim 1, wherein step d) is carried out in an acidic medium with or without an organic solvent at a temperature of 50 to 140 ° C. for a reaction time of 1 to 8 hours.

25. A process according to claim 24, wherein the temperature is 60 to 80° C. and the reaction time is 2 hours.

* * * * *

UNITED STATES PATENT AND TRADEMARK OFFICE
CERTIFICATE OF CORRECTION

PATENT NO. : 7,288,658 B2
APPLICATION NO. : 10/888912
DATED : October 30, 2007
INVENTOR(S) : Goehring et al.

It is certified that error appears in the above-identified patent and that said Letters Patent is hereby corrected as shown below:

Title Page (30):

• The Foreign Application Priority Data reads
"Jul. 15, 2003 (EP).....................0301559". The Foreign Application Priority Data should read -- Jul. 15, 2003 (EP)....................03015599 --.

Signed and Sealed this

Twenty-ninth Day of April, 2008

JON W. DUDAS
*Director of the United States Patent and Trademark Office*